United States Patent
Zhang

(10) Patent No.: US 6,949,258 B2
(45) Date of Patent: Sep. 27, 2005

(54) BIOLOGICALLY ACTIVE ORAL PREPARATION THAT CAN BE SITE-SPECIFIC RELEASED IN COLON

(75) Inventor: Junshou Zhang, Jiangsu (CN)

(73) Assignee: Hao Zhang, Jiangsu (CN)

(*) Notice: Subject to any disclaimer, the term of this patent is extended or adjusted under 35 U.S.C. 154(b) by 305 days.

(21) Appl. No.: 10/297,527

(22) PCT Filed: Jun. 7, 2001

(86) PCT No.: PCT/CN01/00920

§ 371 (c)(1),
(2), (4) Date: Apr. 15, 2003

(87) PCT Pub. No.: WO02/20037

PCT Pub. Date: Mar. 14, 2002

(65) Prior Publication Data

US 2003/0166508 A1 Sep. 4, 2003

(30) Foreign Application Priority Data

Jun. 7, 2000 (CN) .......................... 0117990 A

(51) Int. Cl.⁷ .................................. A61K 9/48
(52) U.S. Cl. ........................................ 424/463; 424/451
(58) Field of Search ................................. 424/451, 463, 424/1.45, 1.61, 1.85

(56) References Cited

U.S. PATENT DOCUMENTS

| 4,652,441 A | * | 3/1987 | Okada et al. |
| 5,840,332 A | | 11/1998 | Lerner et al. ............... 424/464 |

FOREIGN PATENT DOCUMENTS

| CN | 87103560 | 5/1988 |
| CN | 1188642 | 7/1998 |
| EP | 0418642 | 3/1991 |
| EP | 0 888 778 A1 * | 7/1999 |

* cited by examiner

Primary Examiner—Thurman K. Page
Assistant Examiner—Retford Berko
(74) Attorney, Agent, or Firm—Ladas & Parry

(57) ABSTRACT

The invention is directed to an oral biological preparation for specific delivery in colon, especially an oral insulin preparation for specific delivery in colon.

7 Claims, No Drawings

BIOLOGICALLY ACTIVE ORAL PREPARATION THAT CAN BE SITE-SPECIFIC RELEASED IN COLON

FIELD OF THE INVENTION

The invention is directed to an oral biological preparation for specific delivery in colon, especially an oral insulin preparation for specific delivery in colon.

BACKGROUND ART

Biological drugs such as protein or polypeptide drugs, especially oral insulin preparation have been being the subject matter sought to be solved in pharmaceutical field. This is because biological drugs such as insulin by oral administration can not usually be absorbed and the bio-availability thereof is low. At present, biological drugs such as insulin are mainly administrated to patients by injection, which makes patients inconvenient and painful. Therefore, it is necessary to develop protein or polypeptide drugs such as insulin oral preparation.

U.S. Pat. No. 5,840,332 discloses a gastrointestinal delivery system, which comprises a drug in combination with a core material, the core being surrounded by a water-insoluble or relatively water-insoluble coating material, the core material includes calcium pectinate containing 2–4% calcium by weight (see column 15 line 4), gastrointestinal tract includes colon, and the drug contains protein or polypeptide drug such as insulin. However, the prior art does not provide any a specific solution of carrying out release of oral preparation of protein or polypeptide drugs in colon. In addition, it was reported that a proteinase inhibitor as an absorption promoter was used to improve the bio-availability of insulin oral preparation, but the bio-availability of insulin oral preparation obtained is merely 5.73–7.58%, which can not satisfy clinical requirements, and simultaneously long-term use of the proteinase inhibitor may cause the disturbance of gastrointestinal function.

OBJECT OF THE INVENTION

The object of the invention is to seek and develop an oral preparation of protein or polypeptide drugs especially insulin.

BRIEF DESCRIPTION OF THE INVENTION

The inventor has found that protein or polypeptide drug is mixed with an absorption promoter and a stabilizer to form a water-in-oil emulsion or water/oil/water complex emulsion or aqueous solution, then the emulsion or aqueous solution is filled into a specific capsule shell of the invention to obtain the oral biological preparation locally delivered in colon. When the oral biological preparation is an oral insulin preparation, the bio-availability thereof is 18–21% (rat). The reduction rate of blood sugar after delivering the aqueous solution preparation in colon for 0.5 hours is 72.7% . The above discoveries bring the invention to be achieved.

The first aspect of the present invention relates to an oral biological preparation for specific delivery in colon, which comprises: 1) a drug selected from proteins or polypeptides, an absorption promoter and a stabilizer and 2) a specific capsule shell, characterized in that the capsule shell contains a metal salt of pectin containing 5–12% by weight of metal and 6–10% by weight of water.

The invention also relates to an oral insulin preparation for specific delivery in colon, which comprises: 1) insulin, an absorption promoter and a stabilizer and 2) a specific capsule shell, characterized in that the capsule shell contains a metal salt of pectin containing 5–12% by weight of metal and 6–10% by weight of water.

The invention also relates to a capsule shell for specific delivery of drug in colon, characterized in that the capsule shell contains a metal salt of pectin containing 5–12% by weight of metal and 6–10% by weight of water.

The invention also relates to a process for the preparation of the specific capsule shell, which comprises:

1) Mixing lower methoxy-pectin with a cross-linking agent selected from a group consisting of formaldehyde, glutaraldehyde, sodium alginate, gelatin, arabia gum, peach gum, methylcellulose, ethylcellulose, polyvinylpyrrolidone, hydroxypropylmethylcellulose, chitosan or acrylic resin, a plasticizer selected from propylene glycol, glycerin, diethyl phthalate, dibutyl sebate, tributyl citrate or castor oil, and water, holding and degassing at 50° C. to form a glue liquid, 2) Coating clean mold rods with a liquid paraffin as lubricant) then dipping in the glue liquid of step i) for 15 seconds to 1 minute, and drawing out from the glue liquid;

3) Dipping the solidified mold rods of step ii) into an 0.1–10% (w/w) ethanol solution of a metallic salt such as $CaCl_2$ to calcify, and holding at 40–80° C. for 10 minutes to 5 hours;

4) Drying the solidified mold rods of step iii) by air blowing at 30–60° C. and 30–40% humidity until the water content is 6–10 wt %.

5) When necessary, dipping the mold rods of step iv) into a 1–10% (w/v) solution of polyvinylpyrrolidone for a moment, drawing out and drying with hot air, then dipping into a 1–10% (w/v) solution of acrylic resin for a moment, drawing out and drying with hot air, demolding and cutting according to the needed size to obtain said capsule shells.

The invention further relates to a process for the preparation of oral biological preparation, especially oral insulin preparation for specific delivery in colon, comprising mixing protein or polypeptide drugs such as insulin with a pharmaceutically acceptable absorption promoter and a stabilizer, encapsulating into a specific capsule shell. The insulin used in the invention is natural insulin, synthetic insulin, or insulin obtained by genetic engineering.

DETAILED DESCRIPTION OF THE INVENTION

According to the invention, the amount of insulin is 1 Iu/kg to 20 Iu/kg.

According to the invention, the absorption promoter and the stabilizer are selected from sodium cholate, sodium glycyicholate, sodium taurocholate, sodium deoxycholate, capric acid, sodium caprate, caprylic acid, oleic acid, beta-cyclodextrin, $EDTA-Na_2$ hydroxypropyl beta-cyclodextrin, polycarboxyethylene glycol, sodium dodecylsulfate, Brij, Tween, Span, eudesmol, menthol, camphol, muscone, enoxolone, glycyrrhetic acid, azone, propylene glycol, glycerin, ethanol, citric acid, sodium salicylate, PEG, fusidic acid, pyrrolidone, benzyl alcohol, linoleic acid, benzyl benzoate, myristyl myristate or ethyl oleate, and urea, etc.

According to the invention, the metal salt of pectin is selected from calcium pectinate, iron pectinate, or zinc pectinate, preferably calcium pectinate.

According to the invention, the specific capsule shell is preferably calcium pectinate containing 5–12% of calcium.

According to the invention, the oral biological preparation is preferably in the form of capsule.

According to the invention, the oral biological preparation comprises 0.05–20% (w/w) of drug, 5–50% (w/w) of absorption promoter, 0.1–30% (w/w) of stablizer and specific capsule shell.

According to the invention, the oral biological preparation is preferably an oral insulin capsule. When the amount of insulin in the capsule is 1 Iu/kg, the bio-availability of which is 18.6% (rat), when the amount of insulin in the capsule is 5 Iu/kg, the bio-availability is 20.3% (rat).

According to the invention, the preparation contains no proteinase inhibitor, as a result, the oral insulin preparation of the invention may not cause the disturbance of gastrointestinal function, and comparing with control indometacin, the insulin preparation of the invention may not cause injury of colic mucosa, even at a dose of as high as 10 Iu/kg. Therefore, the oral insulin preparation of the invention is safe and effective.

The invention therefore further relates to an oral insulin capsule preparation, which comprises 1–10 Iu/kg of insulin, an absorption promoter, a stabilizer, and a specific capsule shell, wherein the specific capsule shell contains calcium pectinate containing 5–12% by weight of calcium and 6–10% of water by weight.

The following examples further describe the invention, but are not intended to limit the invention in any manner.

EXAMPLE 1

| Insulin microemulsion (W/O type, water-in-oil type) | |
|---|---|
| Component | Amount |
| Oil phase: | |
| Oleic alcohol | 8 g |
| Oleic acid | 2 g |
| Lecithin | 1 g |
| Tween-80 | 4 g |
| Aqueous phase: | |
| Insulin | 6 mg |
| Sodium salicylate | 3 g |
| Sodium deoxycholate | 2 g |
| Phosphate buffer | 3 ml |
| Dilute hydrochloric acid | appropriate amount |

The above insulin was added to the phosphate buffer solution, an appropriate amount of dilute hydrochloric acid was added thereto until the insulin was completely dissolved, and then the sodium salicylate and sodium deoxycholate were added to the solution to obtain the aqueous phase. The lecithin was dissolved in the oleic alcohol, then oleic acid and Tween-80 were added to the solution, stirred to obtain the oil phase. The aqueous phase was added drop-wise to the oil phase under stirring to obtain the insulin microemulsion.

EXAMPLE 2

Insulin Complex Emulsion

The insulin complex emulsion is composed of an oil phase, an inner aqueous phase, and an outer aqueous phase, wherein the oil phase is identical as that of example 1, the inner aqueous phase is consisted of 6 mg of insulin, an appropriate amount of dilute hydrochloric acid, and 30 ml of phosphate buffer, the outer aqueous phase is consisted of 2 g of sodium deoxycholate, 3 g of sodium salicylate, and 50 ml of phosphate buffer. Firstly, insulin microemulsion consisted of oil phase and inner aqueous phase was prepared based on the method as described in example 1, then the so obtained microemulsion was added drop-wise to the outer aqueous phase under stirring to obtain semi-transparent insulin complex emulsion.

EXAMPLE 3

| Insulin aqueous solution | |
|---|---|
| Component | Amount |
| Insulin | 6 mg |
| Sodium deoxycholate | 2 g |
| Sodium salicylate | 3 g |
| Dilute hydrochloric acid | appropriate amount |
| Phosphate buffer | 50 ml |

6 mg of insulin was dissolved in an appropriate amount of dilute hydrochloric acid, and the other components were added thereto to obtain the insulin aqueous solution.

EXAMPLE 4

Preparation of Capsule-Core Contents of Oral Insulin Capsule (1) Component:

| | |
|---|---|
| Insulin | 20 U |
| Eudesmol | 0.2 ml |
| SLS | 50 mg |
| Carbopol 971P | 40 mg |
| Mannitol | 300 mg |

(2) Preparation Process:

Sieving Carbopol 971 with 80 mesh sieve, dissolving said amount of Carbopol 971 (80 mesh passed) in distilled water, adding insulin, eudesmol, SLS, and mannitol to the solution, stirring to dissolve, freeze-drying at −20° C. to −60° C. for 48 hours to obtain the capsule-core contents of the capsule for specific delivery in colon.

EXAMPLE 5

Preparation of Capsule-Core Contents of Oral Insulin Capsule Preparation (1) Component:

| | |
|---|---|
| Insulin | 20 u |
| Sodium caprate | 200 mg |
| Sodium salicylate | 120 mg |
| HPMC(40PC) | 250 mg |

(2) Preparation Process

Sieving HMPC with 80 mesh sieve, dissolving said amount of HPMC(40PC) (80 mesh passed) in distilled water, adding insulin, sodium caprate, and sodium salicylate to the solution, stirring to dissolve, freeze-drying at −20° C. to −60° C. for 48 hours to obtain the core contents of the capsule for specific delivery in colon.

EXAMPLE 6
Preparation of Core Contents of Oral Insulin Capsule Preparation
(1) Component:

| | |
|---|---|
| Insulin | 20 u |
| Enoxolone | 150 mg |
| EDTA-Na$_2$ | 50 mg |
| Carbopol 974P | 50 mg |

(2) Preparation Process

Sieving Carbopol 974P, dissolving said amount of Carbopol 974P(80 mesh passed) in distilled water, adding insulin, enoxolone, and EDTA-Na$_2$ to the solution, stirring to dissolve, absorbing the solution with CaHPO$_4$ (2.4 g) and sodium alginate (1.0 g) to obtain the core contents of the capsule for specific delivery in colon.

EXAMPLE 7
Preparation of Capsule-Core Contents of Oral Insulin Capsule
(1) Component

| | |
|---|---|
| Insulin | 20 u |
| Sodium glycylcholate | 200 ml |
| menthol | 0.4 mg |
| Tween-20 | 0.2 mg |

(2) Preparation Process

Dissolving said amount of insulin and sodium glycocholate in distilled water, adding menthol, Tween-20 to the solution, absorbing the solution with CMC—Ca (2.4 g) and sodium alginate (1.6 g) to obtain the capsule-core contents of the capsule for specific delivery in colon.

In the preparation processes, insulin solution can be prepared into solid which is encapsulable via freeze-drying, vacuum-drying, spray-drying, and absorbing with solid absorbent, etc. The absorbent used generally should be capable to improve stability of insulin, enhance membrane permeability, and good water dispersibility, which is typically CaHPO$_4$, CMC—Ca, sodium alginate, HPC, gelatin, PVP, and surfactant, etc. The absorbent is usually composed of one or several types of the above substances.

EXAMPLE 8
Preparation of Capsule Shell Containing Calcium Pectinate

| Component | Amount |
|---|---|
| 15% water solution of lower methoxy-pectin (LMP) | 100 ml |
| 5% Ethanol-water (7:3) solution of CaCl$_2$ | 100 ml |
| 5% Ethanol solution of PVP | 100 ml |
| 8% Alcohol solution of type-II acrylic resin | 100 ml |

Clean mold rods were coated with liquid paraffin, then dipped into the 15% LMP solution for 30 seconds, drawn out and dipped into 5% ethanol solution of CaCl$_2$ and calcified (60° C.) for 1 hour again, dried by air blowing at 35° C. and RH 35% and dipped again into 5% ethanol solution of PVP for 2 minutes, drawn out and dried by air blowing at 35° C. and RH 35% to nearly dry, dipped into 8% alcohol solution of type-II acrylic resin for 1 minute, drawn out and dried to obtain said calcium pectinate capsule shells.

EXAMPLE 9
Preparation of Capsule Shell Containing Calcium Pectinate

| Component | Amount |
|---|---|
| 15% water solution of lower methoxy-pectin (LMP) | 100 ml |
| Arabia gum or peach gum | 2 g |
| 5% Ethanol-water (7:3) solution of CaCl$_2$ | 100 ml |
| 5% Ethanol solution of PVP | 100 ml |
| 8% Alcohol solution of type-II acrylic resin | 100 ml |

Arabia gum or peach gum was dissolved into the LMP solution, or the LMP and arabia gum or peach gum was independently dissolved into a proper amount of water and then mixed to uniform, and then propylene glycol was added to obtain a glue liquid. The residual processes are identical with those disclosed in example 8.

EXAMPLE 10
Preparation of Capsule Shell Containing Calcium Pectinate

| Component | Amount |
|---|---|
| 15% water solution of lower methoxy-pectin (LMP) | 100 ml |
| Gelatin or methylcellulose or hydroxypropylmethyl cellulose or sodium alginate | 2 g |
| Glycerin | 2 g |
| 5% Ethanol-water (7:3) solution of CaCl$_2$ | 100 ml |
| 5% Ethanol solution of PVP | 100 ml |
| 8% Alcohol solution of type-II acrylic resin | 100 ml |

The capsule shells were prepared by the method of example 9.

EXAMPLE 11
Preparation of Capsule Shell Containing Calcium Pectinate

| Component | Amount |
|---|---|
| 15% Water solution of lower methoxy-pectin (LMP) | 100 ml |
| 5% Ethanol solution of ethylcellulose | 100 ml |
| Diethyl phthalate or dibutyl sebate | 1.5 g |
| 5% Ethanol-water (7:3) solution of CaCl$_2$ | 100 ml |
| 5% Ethanol solution of PVP | 100 ml |

Clean mold rods were coated with liquid paraffin, then dipped into the 15% LMP solution for 1 minute, drawn out and dipped into the 5% CaCl$_2$ ethanol (70%) solution, calcified at 60° C. for 1 hour, dried by air blowing at 35° C. and RH35% to nearly dry, and then dipped into an ethanol solution of ethylcelullose having diethyl phthalate or dibutyl sebate for 30 seconds, drawn out and dried to obtain calcium pectinate capsule shells.

EXAMPLE 12

Effects of the insulin preparation prepared in examples 1–3 on blood sugar in rat after delivery in colon 12 Male rats with weight of 250±50 g were randomly separated into two groups, 6 in each group. After fasting for 12–16 hours, the experiment group were fed with 20 Iu/kg of the insulin preparation prepared in examples 1–3, the control group was fed with same dose of an aqueous solution containing insulin only. Blood sample was obtained from venous plexus of eye fungus of rats in 0, 0.5, 1.0, 2.0, 3.0, and 4.0 hours after administration. The blood sugar value in serum was determined by glucose oxidation method, and the results are as follows:

| Preparation | | Time(h) | | | | | |
|---|---|---|---|---|---|---|---|
| | | 0 | 0.5 | 1.0 | 2.0 | 3.0 | 4.0 |
| Control | Bloodsugar | 120.5 ± 15.7 | 120.2 ± 27.2 | 135.3 ± 37.6 | 141.1 ± 30.8 | 126.4 ± 30.5 | 117.2 ± 20.4 |
| | Reduction rate % | / | 0 | −12.3 | −17.1 | −4.9 | −2.6 |
| Microemulsion | Bloodsugar | 103.7 ± 17.1 | 92.4 ± 21.2 | 90.1 ± 24.8 | 91.6 ± 16.8 | 110.7 ± 25.9 | 133.4 ± 12.2 |
| | Reduction rate % | / | 10.9 | 22.8 | 11.7 | −6.8 | −28.5 |
| Complex emulsion | Bloodsugar | 121.3 ± 29.2 | 46.9 ± 22.7 | 32.5 ± 28.1 | 64.1 ± 29.4 | 87.2 ± 34.9 | 120.7 ± 30.8 |
| | Reduction rate % | / | 69.6 | 73.2 | 47.2 | 28.9 | 0.5 |
| Aqueous solution | Bloodsugar | 109.0 ± 21.4 | 29.8 ± 19.7 | 21.1 ± 16.4 | 49.4 ± 23.2 | 89.8 ± 31.6 | 104.6 ± 27.7 |
| | Reduction rate % | / | 72.7 | 80.6 | 54.5 | 17.5 | 4.0 |

What is claimed is:

1. An oral insulin preparation comprising (a) insulin; (b) a capsule shell comprising calcium pectinate containing 5–12 wt % of calcium, an acrylic resin and 6–10 wt % of water; and (c) a plurality of compounds selected from the group consisting of sodium cholate, sodium glycycholate, sodium taurocholate, sodium deoxycholate, capric acid, sodium caprate, caprylic acid oleic acid, beta-cyclodextrin, EDTA-Na$_2$, hydroxypropyl beta-cyclodextrin, polycarboxyethylene glycol, sodium dodecysulfate, Brij, Tween, Span, Eudesmol, menthol, camphol, muscone, enoxolone, glycyrrhetic acid, azone, propylene glycol, glycerin, ethanol, citric acid, sodium salicylate, PEG, fusidic acid, pyrrolidone, benzyl alcohol, linoleic acid, benzyl benzoate, myristyl myristate, ethyl oleate, and urea.

2. The oral insulin preparation according to claim 1, wherein the content of insulin is from 1 Iu/kg to 10 Iu/kg.

3. The oral insulin preparation according to claim 1, wherein the insulin is present in the capsule shell in a microemulsion.

4. The oral insulin preparation according to claim 1, wherein the insulin is present in the capsule shell in a complex emulsion comprising an oil phase, an inner aqueous phase and an outer aqueous phase.

5. The oral insulin preparation according to claim 1, wherein the insulin is present in the capsule shell in an aqueous solution.

6. A capsule shell for specific delivery of insulin in colon, the capsule shell comprising calcium pectinate containing 5–12% by weight of calcium, an acrylic resin and 6–10% by weight of water.

7. A process for preparation of the capsule shell of claim 6, comprising the steps of:
  1) mixing a lower methoxy-pectin with a cross-linking agent selected from the group consisting of formaldehyde, glutaraldehyde, sodium alginate, gelatin, arabia gum, peach gum, methylcellulose, ethylcellulose, polyvinylpyrrolidone, hydroxypropylmehtylcellulose, chitosan and acrylic resin, a plasticizer selected from the group consisting of propylene glycol, glycerin, diethyl phthalate, dibutyl sebate, tributyl citrate and castor oil, and water to form a mixture, and holding and degassing the mixture at 50° C. to form a glue liquid;
  2) coating clean mold rods with a liquid paraffin as lubricant, then dipping the coated rods in the glue liquid for 15 seconds to 1 minute, and drawing the dipped rods out from the glue liquid to obtain solidified mold rods;
  3) dipping the solidified mold rods into an 0.1–10% (w/w) ethanol solution of CaCl$_2$ to calcify, and holding the calcified rods at 40–80° C. for 10 minutes to 5 hours;
  4) drying the solidified, calcified mold rods by air blowing at 30–60° C. and 30–40% humidity until the mold rods have a water content of 6–10 wt %;
  5) dipping the mold rods of step (4) into a 1–10% (w/v) solution of polyivinylpyrrolidone for a moment, drawing out and drying the mold rods with hot air, then dipping them into a 1–10% (w/v) solution of acrylic resin for a moment, drawing out and drying the mold rods with hot air and demolding and cutting the mold rods to obtain said capsule shell.

\* \* \* \* \*